United States Patent [19]
Germida et al.

[11] Patent Number: 6,015,553
[45] Date of Patent: Jan. 18, 2000

[54] BACILLUS SUBTILIS STRAIN FOR CONTROLLING INSECT AND NEMATODE PESTS

[75] Inventors: James John Germida, Saskatoon, Canada; Sherry Darlene Heins; Denise Carol Manker, both of Davis, Calif.; Desmond Rito Jiménez, Woodland, Calif.; Pamela Gail Marrone, Davis, Calif.

[73] Assignee: AgraQuest, Inc., Davis, Calif.

[21] Appl. No.: 08/916,547

[22] Filed: Aug. 22, 1997

[51] Int. Cl.$^7$ .............................. C12N 1/20; A01N 63/00
[52] U.S. Cl. ................................ 424/93.462; 435/252.31; 435/252.5
[58] Field of Search ........................... 435/252.31, 252.5; 424/93.462

[56] References Cited

U.S. PATENT DOCUMENTS

| | | |
|---|---|---|
| 4,999,192 | 3/1991 | Payne et al. . |
| 5,187,091 | 2/1993 | Donovan et al. . |
| 5,208,017 | 5/1993 | Bradfisch et al. . |
| 5,378,460 | 1/1995 | Zuckerman et al. . |
| 5,632,987 | 5/1997 | Payne et al. . |
| 5,645,831 | 7/1997 | Chilcott et al. . |
| 5,733,544 | 3/1998 | Marrone et al. . |

FOREIGN PATENT DOCUMENTS

WO 96/10083   4/1996   WIPO .

OTHER PUBLICATIONS

Johnson et al. (1993) "Insecticidal Activity of EG4961, a Novel Strain of *Bacillus thuringiensis* Toxic to Larvae and Adults of Southern Corn Rootworm (Coleoptera: Chrysomelidae) and Colorado Potato Beetle (Coleoptera: Chrysomelidae)," *J. Ecomonic Entomology* 86:330–333.

Estruch et al. (1997) "Transgenic Plants: An Emerging Approach to Pest Control," *Nature Biotechnology* 15:137–141.

Burgjeron and Biache (1966) "Alimentation Au Laboratoire de Perillus Bioculatus Fabr. Avec des Larves de Leptinotarsa Decemlineat A Say Intoxiquées Par la Toxine Thermostable de *Bacillus thuringiensis* Berliner," *Entomophaga* II:279–284. An English summary is printed on p. 283.

Argauer et al. (1991) "Evidence for a Novel Insecticidally Active Exotoxin Produced by the HD 116 Strain of *Bacillus*," *J. Entomol. Sci.* 26:205–213.

Lüthy (1980) "Insecticidal Toxins of *Bacillus thuringiensis*," *FEMS Mirobiol. Lett.* 8:1–7.

Forsberg et al. (1976) "*Bacillus thuringiensis*: Its effects in Environmental Quality," National Research Council of Canada, NRC Associate Committee on Scientific Criteria for Environmental Quality, NRC 15385, 16 pages total.

Stonard et al. (1994) "Microbial Secondary Metabolites as a Source of Agrochemicals," ACS Symposium Series, Natural and Engineers Pest Management Agents 551:25–35.

Miller (1982) "Single Derivatization Method for Routine Analysis of Bacterial Whole Cell Wall Fatty Acid Methyl esters, Including Hydroxy Acids," *J. Clin Micriobiol.* 16:584–586.

Bochner (1989) "Sleuthing Out Bacterial Identities," *Nature* 339:157–158.

Yu et al. (1997) "The *Bacillus thuringiensis* Vegetative Insecticidal Protein Vip3 Lyses Midgut Epithelium Cells of Susceptible Insects," *Appl. Environ. Microbiol.*, 63:532–536.

Marrone et al. (1985) "Improvements in Laboratory Rearing of the Southern Corn Rootworm, *Diabrotica undecimpuncta howardi* Barber (Coleoptera: Chrysomelidae), on an Artificial Diet and Corn," *J. Econ Entomol.* 78:290–293.

*Primary Examiner*—Herbert J. Lilling
*Attorney, Agent, or Firm*—Antoinette F. Konski; Baker & McKenzie

[57] ABSTRACT

A novel strain of *Bacillus subtilis* is provided that produces a metabolite that exhibits pesticidal activity. Also included in the invention is a solvent extractable and water soluble, large molecular weight (>10,000 daltons) metabolite produced by the novel strain of *Bacillus subtilis* that exhibits pesticidal activity against corn rootworms, other insects and nematodes. Also included in the invention are methods of protecting or treating plants from corn rootworm, other insect and nematode infestations comprising applying to the plant an effective amount of the novel Bacillus strain, a supernatant obtained from a whole broth culture of the novel strain, the metabolite produced by the novel Bacillus strain, a composition comprising the novel strain or a combination thereof, optionally further comprising applying at least one additional biological or chemical pesticide.

9 Claims, 2 Drawing Sheets

```
Sherlock Version: 1.06        AQ743            DATA:C969051308    05-Sep-96 13:13:24
------------------------------------------------------------------------------------
ID:    2606    WHEAT 3-TV5A (from frozen)         Date of run: 05-Sep-96 12:48:30
Bottle: 22     SAMPLE      [AEROBE]

RT      Area     Ar/Ht Respon   ECL      Name          %       Comment 1          Comment 2
  -----  --------   ----- ------  ------  ---------      -----   -----------------  -----------------
  1.493  339435000  0.023  ...    7.020   SOLVENT PEAK .......   < min rt
  7.350       1554  0.036  0.969 14.621   15:0 ISO ......13.33   ECL deviates -0.000 Reference -0.003
  7.479       5136  0.035  0.966 14.711   15:0 ANTEISO....43.92  ECL deviates  0.000 Reference -0.003
  8.875        648  0.032  0.941 15.627   16:0 ISO ......  5.40  ECL deviates  0.001 Reference -0.002
  9.459        960  0.041  0.933 15.999   16:0 .........  7.93   ECL deviates -0.001 Reference -0.004
 10.502       1308  0.040  0.920 16.630   17:0 ISO ...... 10.65  ECL deviates  0.001 Reference -0.003
 10.653       2310  0.042  0.919 16.721   17:0 ANTEISO... 18.78  ECL deviates -0.001 Reference -0.005
 15.733        876  0.215  ...   19.718   ............    ...   > max ar/ht
 16.230        510  0.128  0.870 20.011   20:0 ........   0.00  > max ar/ht Solvent Ar  Total Area  Named Area  % Named  Total Amnt  Nbr Ref   ECL Deviation   Ref ECL Shift
----------  ----------  ----------  -------  ----------  -------   -------------   -------------
339435000      13302      11916      89.58     11299        6          0.004           0.004
* QUESTION ANALYSIS: TOTAL AREA LESS THAN 50000.    CONCENTRATE AND RE-RUN.
-------------------------------------------------------------------------------------
        TSBA [Rev 3.80] Bacillus ................. 0.299
                        B. subtilis  .............. 0.299
                        B. atrophaeus ............ 0.212 (was B. subtilis variety niger)
                        B. licheniformis .......... 0.188 (Bacillus subtilis group)
        CLIN [Rev 3.80]  * NO MATCH *
        RHIZ-1 [Rev 1.0] * NO MATCH *
```

FIG. 1

BACILLUS SUBTILIS STRAIN FOR CONTROLLING INSECT AND NEMATODE PESTS

FIELD OF THE INVENTION

This invention is in the field of biopesticides. More particularly, the present invention describes a novel strain of Bacillus subtilis that exhibits pesticidal activity against corn rootworm (e.g., Diabrotica virgifera, D. longicornis, D. undecimpunctata), beet armyworn (Spodoptera exigua), adult flies (Drosophila melanogaster) and a free-living nematode (Coenorhabditis elegans). The Bacillus sp. strain also produces a secondary metabolite in supernatant that can be used as a biocontrol agent in the treatment and prevention of corn rootworm infestation of plants.

BACKGROUND OF THE INVENTION

Every year 250–300 million dollars of chemical pesticides are used to control corn rootworm infestations. Many of these chemical pesticides are toxic to humans, wildlife and other nontarget species. In addition, some of these pesticides have been found in ground water. New chemical pesticides cost $100 million to develop.

Biological control offers an attractive alternative to synthetic chemical pesticides. Biopesticides (living organisms and the naturally-occurring compounds produced by these organisms) can be safer, more biodegradable, and less expensive to develop.

One commonly used biopesticide is the gram positive bacterium Bacillus thuringiensis. Pesticidal B. thuringiensis strains are known to produce crystal proteins during sporulation, which are specifically toxic to certain orders and species of insects and nematodes (See, e.g., U.S. Pat. No. 4,999,192 and U.S. Pat. No. 5,208,017). Proteinaceous endotoxins produces by B. thuringiensis also act as insecticidal agents against corn rootworm and other beetles (e.g., U.S. Pat. No. 5,187,091; Johnson et al. (1993) J. Economic Entomology 86: 330–333). B. thuringiensis endotoxins have been shown to be effective pesticides in the form of purified crystals, washed cell pellets, and expressed proteins. Warren et al. (WO 96/10083), discloses non-endotoxin proteins produced during the vegetative stage of Bacillus cereus and B. thuringiensis. These vegetative proteins, designated Vip1 and Vip2, have potent activity against corn rootworm (northern and western) (Estruch et al. (1997) Nature Biotechnology 15: 137–141 and Mullins et al. (1997) Appl Environ. Microbiol. 63 (in press).

One B. thuringiensis thermostable metabolite designated beta-exotoxin has also been shown to have pesticidal properties. Burgjeron and Biache (1979) Entomophaga 11: 279–284 report a beta exotoxin that is active against Colorado potato beetle (Leptinotarsa decemlineata). In addition, the known B. thuringiensis beta-exotoxins exhibit non-specific pesticidal activity, killing not only nematodes, but also flies, armyworms, mites, and corn rootworms. Sigma-exotoxin has a structure similar to beta-exotoxin, and is active against Colorado potato beetle (Argauer et al. (1991) J. Entomol. Sci. 26: 206–213). Alpha-exotoxin is toxic against larvae of Musca domestica (Cluthy (1980) FEMS Microbiol. Lett. 8: 1–7). Gamma-exotoxins are various proteolytic enzymes, chitinases and proteases. The toxic effects of gamma-exotoxins are only expressed in combination with beta-exotoxin or delta-endotoxin. Forsberg et al. (1976) "Bacillus thuringiensis: Its effects in Environmental Quality," National Research Council of Canada. Stonard et al. (1994) ACS Symposium Series 551: 25 report a water-soluble secondary metabolite exhibiting pesticidal activity against corn rootworm in the supernatant of a Bacillus cereus strain.

There are no documented strains of Bacillus subtilis with pesticidal activity against coin rootworm. There are no known metabolites from Bacillus subtilis with pesticidal activity against corn rootworm.

BRIEF DESCRIPTION OF THE DRAWINGS

FIGS. 1 and 2 show the MIDI profiles obtained for AQ743.

DISCLOSURE OF THE INVENTION

Figure 2:
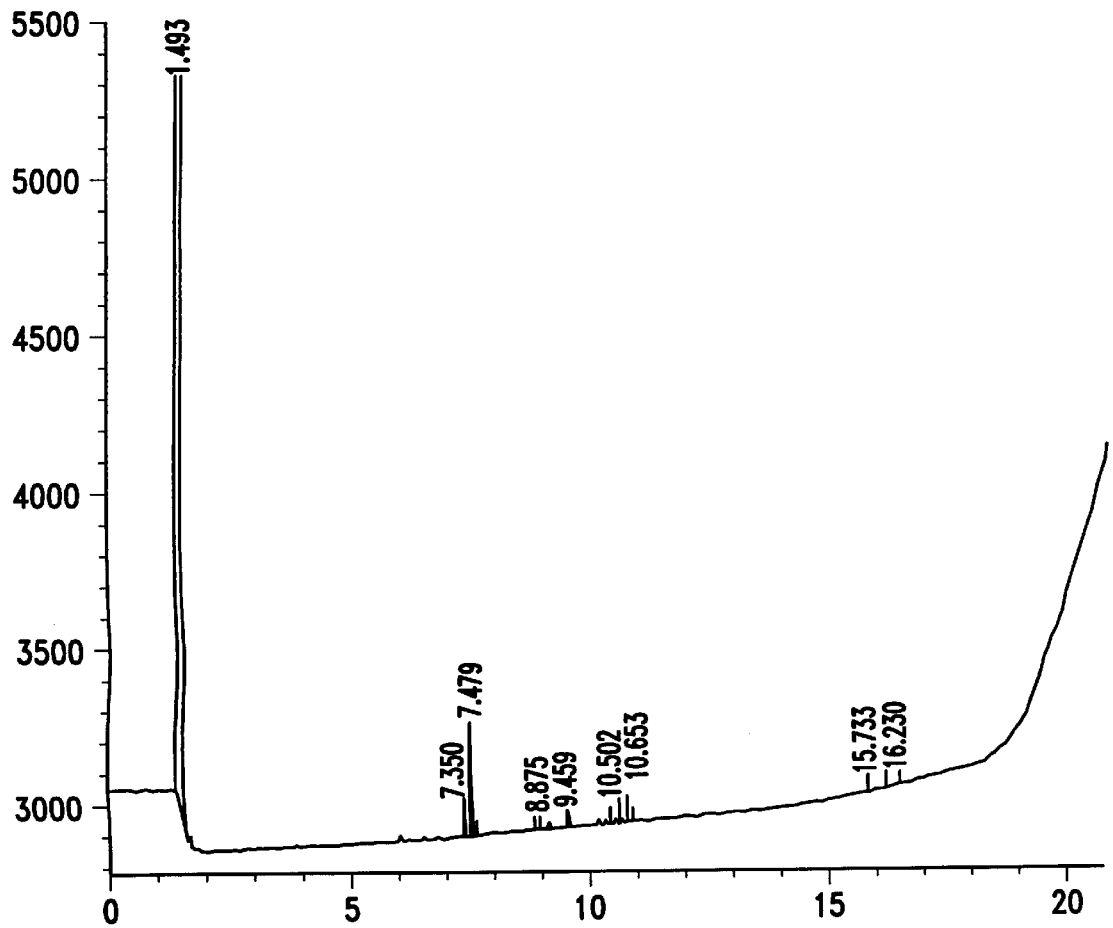

A novel strain of Bacillus subtilis strain AQ743, is provided that produces a metabolite that exhibits pesticidal activity against corn rootworm. Also provided is a novel metabolite produced by the novel B. subtilis strain that exhibits pesticidal activity against corn rootworm and other insects. Also provided is a method of treating or protecting plant roots from coin rootworm infestations comprising applying an effective amount of the novel metalolite-producing B. subtilis strain, a supernatant obtained from a whole broth culture containing the metabolite produced by the bacterial strain, or the metabolite itself.

MODES OF CARRYING OUT THE INVENTION

The present invention provides a novel strain of Bacillus subtilis isolated from wheat roots or mutants and variants thereof that produce a metabolite with anti-corn rootworm activity. This novel strain is designated AQ743, and was deposited with the Agriculture Research Culture Collection (NRRL) having a place of business at 1815 N. University Street, Peoria, Ill. 610604, U.S.A., on Mar. 7, 1997 under the provisions of the Budapest Treaty on the International Recognition of the Deposit of Microorganisms for the Purpose of Patent Procedure under Accession No. B-21665. The invention also includes methods of protecting or treating plants and their environments from corn rootworm larvae by applying an effective amount of a bacterial suspension of AQ743, a metabolite-containing supernatant of a whole broth culture of AQ743, or the purified metabolite produced by strain AQ743 and, optionally, further comprising applying at least one additional biological or a chemical pesticide. The invention also includes a water soluble metabolite produced by the novel B. subtilis strain.

Difinitions

As used herein, "biological control" is defined as control of a pathogen or insect by the use of a second organism.

The term "bacteria" includes any prokaryotic organism that does not have a distinct nucleus.

The term "culturing" refers to the propagation of organisms on or in media of various kinds.

"Whole broth culture" refers to a liquid culture containing both cells and media.

"Supernatant" refers to the liquid broth remaining when cells grown in broth are removed by centrifugation, filtration, sedimentation, or other means well known in the art.

An "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the insect infestation.

As used herein, the term "insects" includes all organisms in the class "Insecta."

"Pre-adult" insects refers to any form of an organism prior to the adult stage, including, for example, eggs, larvae, and nymphs.

"Insecticidal" refers to the ability of a substance to increase mortality or inhibit growth rate of insects.

"Nematicidal" refers to the ability of a substance to increase mortality or inhibit the growth rate of nematodes.

"Pesticidal" refers to the ability of a substance to increase mortality or inhibit the growth rate of insects, nematodes and mites.

"Positive control" means a compound known to have pesticidal activity. "Positive controls" include, but are not limited to commercially available chemical pesticides.

The term "negative control" means a compound known not to have pesticidal activity. Examples of negative controls are water or acetone.

The term "solvent" includes any liquid that holds another substance in solution. "Solvent extractable" refers to any compound that dissolves in a solvent and which then may be isolated from the solvent. Examples of solvents include, but are not limited to, organic solvents like ethyl acetate or acetone.

The term "metabolite" refers to any compound, substance or byproduct of a fermentation of a microorganism that has pesticidal activity.

We describe a novel metabolite-producing bacterial strain of *Bacillus subtilis* that kills or stunts corn rootworm larvae, beet armyworm larvae, fly adults and nematodes.

In another aspect, the present invention provides a method of treating or protecting plants from corn rootworm, nematode and armyworm infestations comprising applying an effective amount of a supernatant obtained from a whole broth culture of *Bacillus subtilis* AQ743 to the plant and its environment. The supernatant may be obtained by methods well known in the art including centrifugation, filtration, sedimentation and the like.

In another aspect, the invention encompasses a method of treating or protecting plants from corn rootworm, nematode and armyworm infestations comprising applying an effective amount of a whole broth culture of the novel strain of *Bacillus subtilis* to the plant and its environment.

In yet another aspect, the invention encompasses a method of treating or protecting plants from corn rootworm, nematode and armyworm infestations comprising applying an effective amount of a composition comprising the novel strain of *Bacillus subtilis* to the plant and its environment.

In further aspect, the invention encompasses a method of treating or protecting plants from corn rootworm, nematode and armyworm infestations comprising applying an effective amount of the metabolite produced by the novel strains of *Bacillus subtilis* to the plant and its environment.

In yet a further aspect, the invention encompasses the foregoing methods of treating or protecting plants from corn rootworm, other insects and nematodes, and optionally, further comprises applying at least one additional biological or chemical pesticide.

In order to achieve good dispersion and adhesion of the supernatant, whole broth culture, metabolite and composition within the present invention, it may be advantageous to formulate the whole broth culture, supernatant, metabolite or composition with components that aid dispersion and adhesion. Suitable formulations will be known to those skilled in the art.

Compositions, supernatants, whole broth cultures and metabolites within the present invention can be formulated as wettable powders, granules and the like, or can be microencapsulated in a suitable medium and the like. Examples of other formulations include, but are not limited to soluble powders, wettable granules, dry flowables, aqueous flowables, wettable dispersible granules, emulsifiable concentrates and aqueous suspensions. Other suitable formulations will be known to those skilled in the art.

All patents and publications cited herein are incorporated by reference. The following examples are provided to illustrate the invention. These examples are not to be construed as limiting.

EXAMPLES

Example 1

Characterization of Strain AQ743

Isolates were identified based on whole-cell cellular fatty acids, derivatized to methyl esters (FAMEs) (Miller, L. T. (1982) "Single derivatization method for routine analysis of bacterial whole cell wall fatty acid methyl esters, including hydroxy acids," *J. Clin. Microbiol.* 16: 584–586) and analyzed by gas chromatography using the MIDI system (Microbial Identification System, Inc., Newark, Del). The procedure and protocols used for growing the bacterial cultures and instrument specification are described by MIDI (Identification of bacteria by gas chromatography of cellular fatty acids. Technical Note #101. MIDI Inc., Newark, Del.) Isolates were grown on tryptic soy agar (TSA) (BBL) plates at 28° C. for 24 hours and cells harvested. One mL of a methanolic NaOH (15% [wt/vol] NaOH in 50% [vol/vol] methanol) was added and cells were saponified at 100° C. for 30 minutes. Esterification of fatty acids was performed with 2 mLs of 3.25 N HCl in 46% (vol/vol) methanol at 80° C. for 10 minutes. The FAMEs were extracted into 1.25 mL of 1:1 (vol/vol) methyl-tert-butyl ether-hexane, and the organic extract washed with 3 mL of 1.2% (wt/vol) NaOH before analysis by gas chromatography. The GC (Hewlett-Packard 5890A) was equipped with a flame ionization detector and capillary column (Hewlett-Packard No. 19091B-102 (Cross-linked 5% phenyl-methyl silicone; 25 m×0.22 mm ID; film thickness, 0.33 $\mu$m; phase ratio, 150) with hydrogen as the carrier gas. FAME peaks were automatically integrated by a Hewlett-Packard 3392 integrator and bacterial isolates named using the MIDI Microbial Identification Software (Sherlock TSBA Library version 3.80). The FAME profile of *Xanthomonas maltophila* ATCC 13637 was used as reference check for the MIDI determinations. The actual MIDI profiles of the strain are shown in FIGS. 1–2. AQ743 was identified as *Bacillus subtilis* in two separate MIDI runs with a similarity index of 0.300 and 0.299.

The isolate was also identified based on utilization of the Biolog microplate panel (Biolog, Inc., Hayward, Calif.) as described in Bochner (1989) *Nature* 339: 157–158. The Biolog microplate is comprised of prefilled and dried panel wells with 95 different carbon substrates) plates available for gram positive and gram negative bacteria). The isolate was grown in liquid medium at 28° C. and after 24 hours a washed cell suspension (0.85% saline) was inoculated into each panel well of a GP Microplate (Biolog, Inc.) After 24 hours at 28° C., carbon utilization reactions were assessed. Substrate utilization profiles were then compared to the Biolog Gram-Positive Data Base (release 3.50) and isolated to closest similar species. Biolog results gave a similarity index of 0.566 to *Bacillus subtilis*.

Example 2
Activity of AQ743 Against Corn Rootworm

Samples of the novel strain were grown in two different Bacillus culture media, called medium 2 and medium 3. Medium 2 contained 5 g dextrose, 5 g peptone., 3 g yeast extract, 1.5 g proflo (cottonseed flour), 10 g soy flour, 0.5 g $MgSO_4 \cdot 7H_2O$, Medium 3 contained 3 g dextrose, 20 g peptone, 3 g yeast extract, 1.5 g proflo (cottonseed flour), 5 mLs of a solution (3.66 g $CaCl_2 \cdot 2H_2O$ per 100 mLs), 5 mLs of a salt solution (2.46 g $MgSO_4 \cdot 7H_2O$, 0.046 g $MnCl_2$, 0.28 g $ZnSO_4 \cdot 7H_2O$, 0.4 g $FeSO_4 \cdot 7H_2O$ per 100 mLs), 3.4g $KH_2PO_4$ and 4.35 g $K_2HPO_4$. One day old streaked cultures were used to inoculate 250 mL baffled shake flasks. Flasks were shaken at 210 rpm at 29° C. for 3 days. To assay insecticidal activity, 5 mLs of culture broth were centrifuged at 5,200 rpm for 20 minutes and the supernatant used in microassay described below.

Assays were performed in 96-well microplates. Each well contained a solid agar substrate, a test organism and either a positive control, a negative control or supernatant obtained as described in Example 1 from the novel strain.

To assay pesticidal activity, an agar substrate was prepared for the wells of the microplate according to Marrone et al. (1985) *J. Econ. Entomol.* 78:290–293. To assay nematicidal activity, plain agar (1.5%) was used in the wells instead.

A 1 ppm solution of Avid® (avermectin) was used as a positive control. Deionized water was used as a negative control. Two replicates of test sample or control were used for each assay. 40 uL of supernatant sample or whole broth grown in medium 2 or 3 were dispensed into each sample well. Plates were then placed in a fume hood to dry for approximately 2–3 hours until the agar solution was dried.

Test organisms were either pre-adult corn rootworms (*Diabrotica undecimpunctata*), pre-adult German cockroaches (*Blatella germanica*), pre-adult beet armyworms (*Spodoptera exigua*), adult flies (*Drosophila melanogaster*), or the N2 strain of the nematode *Caenorhabditis elegans*. Test organisms were diluted in 0.1% agar to a concentration of approximately 5 organisms per 25 μL of agar dispensed into each well. The microplate was sealed with an airtight substance such as Mylar®, and each well ventilated with a pin press. The plates were incubated at 27° C. for up to 7 days.

After incubation, wells were scored by noting neonate mortality or the degree of larval development. Sample wells containing all dead or stunted larvae were given a score of 1, wells containing some dead and other severely stunted larvae were given a score of 2, live but stunted larvae were scored as 3 and sample wells containing no dead larvae were given a score of 4. Scores were averaged among replicates within each sample. Results are summarized in Tables 1–3.

TABLE 1

Score Rating of AQ743 Medium 2

|  | C. elegans | Corn rootworm | Beet armyworm | Fruit Fly | German Cockroach | Positive Control | Negative Control |
| --- | --- | --- | --- | --- | --- | --- | --- |
| Supernatant | 4.0 | 1.0 | 1.0 | NT | 4.0 | 1.0 | 4.0 |
| Whole Broth | 4.0 | 1.0 | 3.0 | 3/4* | 4.0 | 1.0 | 4.0 |

NT=Not Tested

*3 rating against adults, 4 rating against larvae that grew from eggs laid by surviving adult flies In Medium 2, the supernatant of AQ743 had strong activity against corn rootworm and beet armyworm and slight activity against adult flies.

TABLE 2

Score Rating of AQ743 Medium 3

|  | C. elegans | Corn rootworm | Beet armyworm | Fruit Fly | German Cockroach | Positive Control | Negative Control |
| --- | --- | --- | --- | --- | --- | --- | --- |
| Supernatant | 3.0 | 2.0 | 2.0 | NT | 4.0 | 1.0 | 4.0 |
| Whole Broth | 4.0 | 2.0 | 3.0 | 3/4* | 4.0 | 1.0 | 4.0 |

NT=Not Tested

*3 rating against adults, 4 rating against larvae that grew from eggs laid by surviving adult flies In Medium 3, the supernatant of AQ743 had strong activity against corn rootworm and beet armyworm and slight activity against adult flies.

Example 3
Chemical Properties of the AQ743 Metabolite that Exhibits Pesticidal Activity Against Corn Rootworm To determine if the metabolite produced by AQ743 is extractable in ethyl acetate, 50 mLs of a culture of AQ743 was grown in medium 2.50 mLs of ethyl acetate was added to each 50 mL culture and the mixture was shaken in a separatory funnel for 2 minutes. The aqueous layer was removed and the organic layer was collected in a bottle containing magnesium sulfate. The organic filtrate was then filtered into a round bottom flask and the solvent removed on the rotovap.

For the bioassay, the dried organic extract was redissolved in 2.5 mLs acetone. A 40 μL aliquot was removed and diluted to 800 μL with 70% acetone/water. This is a 10× concentration of the organic extract. Serial dilutions were carried out to obtain samples on neonate corn rootworm with percent mortality recorded of neonate larvae (1 per well in a microplate as prepared above) after 7 days. The results are recorded in Table 4.

TABLE 4

Activity of Ethyl Acetate Extract of AQ743 Against Corn Rootworm

| Sample | | Percent Mortality | |
| --- | --- | --- | --- |
| AQ743: | Organic extract 10X | 73 | |
|  | Organic extract 5X | 69 | |
|  | Organic extract 2.5X | 64 | |
|  | Organic extract 1.0X | 55 | |
|  | Aqueous 2.0X | | 100 |
|  | Aqueous 1X | | 88 |
|  | 75% acetone/water | 42 | 44 |
|  | Water | 21 | 57 |

Not Tested

The results show that the metabolite produced by AQ743 that exhibits pesticidal activity against corn rootworms has water soluble and also solvent-extractable properties.

Example 4
Molecular Weight Cutoff Experiment

To determine the molecular weight range of the active metabolite, a 50-mL culture of AQ726 was grown in medium 2. One mL of the culture was placed into a microfuge tube and spun at 12,000 rpm for 15 minutes. The supernatant was removed. 500 microliters of supernatant were placed on top of a 10,000 dalton molecular weight centricon filter. These were centrifuged according to the manufacturer's instructions (12,000 rpm for 35 minutes). The filtrate was collected and the retentate recovered by centrifugation and washing of the filter. Samples of the supernatant, filtrate and retentate were tested against neonate corn rootworm larvae (96-well microplate with insect diet, Marrone et al., supra as above; 40 μLs of sample per well and 8 wells for each sample, 1 larva/well). The results of the test are shown in Table 5.

TABLE 5

Molecular Weight Cutoff of AQ743
Percent Mortality Against Corn Rootworm

|  | Test 1 | Test 2 |
| --- | --- | --- |
| supernatant | 13 (severe stunt) | 83 |
| filtrate | 29 | 33 |
| retentate | 100 | 88 |
| water control | 0 | 29 |

The results show that the supernatant and retentate were active, thus the molecular weight of the metabolite is greater than 10,000 daltons.

What is claimed is:

1. An isolated, pure culture of Bacillus strain AQ743, NRRL Accession No. B-21665, having pesticidal activity, and mutants thereof, which mutants maintain the pesticidal activity.

2. A composition comprising the Bacillus strain of claim 1 that exhibits pesticidal activity against corn rootworm, nematodes and beet armyworm.

3. A method for protecting or treating a plant from corn rootworm, other insect and nematode infestations comprising applying an effective amount of the *Bacillus subtilis* strain of claim 1 to the plant or its environment.

4. A method of claim 2 wherein the Bacillus is applied as a whole broth culture.

5. A method for protecting or treating a plant from corn rootworm, other insect and nematode infestations comprising applying an effective amount of the composition of claim 2.

6. The method of claim 3 further comprising at least one chemical or at least one additional biological pesticide.

7. The method of claim 5 further comprising applying at least one additional chemical or biological pesticide.

8. The method of claim 3, wherein the Bacillus is applied as a wettable powder, granule, flowable or microencapsulation.

9. The method of claim 5, wherein the supernatant is applied as a wettable powder, granule, flowable or microencapsulation.

* * * * *

UNITED STATES PATENT AND TRADEMARK OFFICE
CERTIFICATE OF CORRECTION

PATENT NO.   : 6,015,553
DATED        : January 18, 2000
INVENTOR(S)  : Germida et al.

It is certified that error appears in the above-identified patent and that said Letters Patent is hereby corrected as shown below:

Title page,
Item [73], The University of Saskatchewan should be listed in addition to AgraQuest, Inc.

Column 1,
Line 36, "produces" should be -- produce --;
Line 51, "*Entamorhaga*, 11:279-284" should be -- *Entophomaga* II:279-284 --;
Line 59, "206-213" should be -- 205-213 --;
Line 60, "Cluthy" should be -- Lüthy --.

Column 2,
Line 21, "coin" should be -- corn --;
Line 34, "610604" should be -- 61604 --;
Line 48, "Difinitions" should be -- Definitions --.

Column 7, claim 1,
The claim should read -- 1. An isolated, pure culture of *Bacillus* having all the identifying characteristics of strain AQ743, NRRL Accession No. B-21665, and mutants thereof, said pure culture and mutants exhibiting pesticidal activity against corn rootworm, nematodes and beet armyworm. --

Signed and Sealed this

Twenty-fifth Day of December, 2001

Attest:

*Attesting Officer*

JAMES E. ROGAN
*Director of the United States Patent and Trademark Office*